United States Patent
Factor et al.

(12) 
(10) Patent No.: US 6,258,042 B1
(45) Date of Patent: Jul. 10, 2001

(54) VISUAL ANALOG SCALE AND METHOD OF USE FOR THE DIAGNOSIS AND/OR TREATMENT OF PHYSICAL PAIN

(76) Inventors: James S. Factor, 606 N. Trenton Dr., Beverly Hills, CA (US) 90210; Harald Azuma, 36502 Clearwood Ct., Palmdale, CA (US) 93550

( * ) Notice: Subject to any disclaimer, the term of this patent is extended or adjusted under 35 U.S.C. 154(b) by 0 days.

(21) Appl. No.: 09/398,358

(22) Filed: Sep. 17, 1999

(51) Int. Cl.[7] .................................................. A61B 19/00
(52) U.S. Cl. .............................................................. 600/557
(58) Field of Search ..................................... 600/557, 553, 600/552, 555

(56) References Cited

U.S. PATENT DOCUMENTS

| | | |
|---|---|---|
| 3,722,796 | 3/1973 | Fleming . |
| 4,071,189 | 1/1978 | Qureshi . |
| 4,337,391 | 6/1982 | Lampert . |
| 4,960,029 | 10/1990 | Nelson . |
| 5,018,526 | 5/1991 | Gaston-Johansson . |
| 5,485,852 | 1/1996 | Johnson . |
| 5,533,514 | 7/1996 | Lavigne . |
| 5,634,472 | 6/1997 | Raghuprasad . |
| 5,653,739 | 8/1997 | Maurer . |
| 5,692,500 | 12/1997 | Gaston-Johansson . |
| 5,873,900 | 2/1999 | Maurer . |

*Primary Examiner*—Eric F. Winakur
*Assistant Examiner*—Pamela L Wingood
(74) *Attorney, Agent, or Firm*—Joseph A Yanny; Michael A DiNardo

(57) ABSTRACT

The present invention is directed toward an apparatus and method for the accurate and uniform diagnosis and/or treatment of varying forms of pain that a person is experiencing. The apparatus is a hand-held device displaying two complimentary scales on opposite faces bearing a slidable indicator that a person can use to describe the amount and intensity of the pain that he/she is experiencing. One side of the device displays a patient's pain scale that depicts a spectrum of pain ranging from no pain to unbearable pain. The other side of the device displays a provider's pain scale divided into discrete intervals identifying verbal and/or numerical pain descriptors. The slidable indicator is mounted on the device and overlays both scales on each side of the panel. The slidable indicator has an indicator line for each scale. The indicator lines are arranged such that when one indicator line is moved, the other indicator line is moved in a complimentary manner. The method of use provides that a patient indicate the amount of pain being experienced on the patient's pain scale using the slidable indicator. The patient is not permitted to view the provider's pain scale. A health care provider then reads and records the numerical and/or verbal pain descriptor indicated on the provider's pain scale by the slidable indicator.

21 Claims, 2 Drawing Sheets

VISUAL ANALOG SCALE AND METHOD OF USE FOR THE DIAGNOSIS AND/OR TREATMENT OF PHYSICAL PAIN

CROSS-REFERENCE TO RELATED APPLICATION

Not Applicable.

STATEMENT RE: FEDERALLY SPONSORED RESEARCH AND DEVELOPMENT

Not Applicable.

BACKGROUND OF THE INVENTION

Healthcare providers are constantly faced with the problem of diagnosing and treating patients suffering from varying levels of pain. Difficulty in properly diagnosing and treating the varying levels of pain results from the patients' inability to accurately describe the pain that they are experiencing. The lack of a uniform system for the patients to use in describing the pain often presents a healthcare provider with very different descriptions for the same levels of pain. These different descriptions sometimes result in ineffective, inadequate or excessive treatments. In addition, the lack of a uniform system for the patients to use in describing their pain results in an inaccurate medical record and an inability to describe the pain and course of treatment accurately for insurance providers.

Traditionally, healthcare providers have used varying devices/methods for measuring the amount and/or intensity of pain that a patient is suffering. The predominant device/method has been categorical pain descriptors, both verbal and/or numerical (i.e. none, mild, moderate, and severe; or 0 through 3). Other devices/methods have employed visual analog scales (VAS) displaying a scale bearing the same or similar verbal and/or numerical categorical pain descriptors. In using either of these devices/methods the healthcare provider asks the patient to describe the pain using the categorical descriptors by presenting the categories to the patient either through oral description or by VAS.

By virtue of the categorical limitations inherent in these devices/methods, a healthcare provider inevitably encounters varying descriptions of the same levels of pain intensity from patient to patient. In the above methods, the categorical descriptors presented by a health care provider may influence a patient. The health care profession is constantly looking for new and better methods to properly diagnose the amount and intensity of pain that a patient is experiencing.

Therefore, it is an object of this invention to provide an improved device by which a health care professional can diagnose the amount and intensity of pain that a patient is experiencing.

It is another object of this invention to provide an improved method by which the health care profession can diagnose the amount and intensity of pain that a patient is experiencing.

It is a further object of this invention to provide a device that can diagnose the amount of pain that a patient is experiencing without suggesting categorical descriptors to the patient that can influence the patient's disclosure.

It is still a further object of this invention to provide a device by which a health care provider can more accurately diagnose the amount and intensity of pain that a patient is experiencing for a more complete and accurate medical record.

BRIEF SUMMARY OF THE INVENTION

The present invention is directed toward an apparatus and method for the accurate and uniform diagnosis and/or treatment of varying forms of pain that a person is experiencing. More particularly, the present invention is directed toward a measurement device displaying two complimentary scales and bearing a slidable indicator that a person can use to describe the amount and intensity of the pain that the person is experiencing.

The apparatus for the diagnosis and/or treatment of pain is a handheld device in the shape of a two-sided rectangular panel. One side of the panel bears a patient's pain scale that depicts a spectrum of pain ranging from no pain to unbearable pain. The scale is an uninterrupted line that bears no indicators or markings other than at the ends indicating no pain or unbearable pain.

The other side of the panel bears a provider's pain scale divided into discrete intervals numbered 0 through 10. The discrete intervals in turn represent increasing levels of pain described using terms ranging from "no pain" to "constant severe pain." The discrete intervals correspond to terms used by providers and insurers to identify and treat pain.

The apparatus is provided with an indicator slidably mounted on the panel that wraps around the panel and overlays both scales on each side of the panel. The indicator bears indicator lines that point to specific points along each scale. Each indicator line is connected to the other, such that when one indicator line is moved, the other indicator line is moved in a complimentary manner.

The patient's pain scale and the provider's pain scale are lined up on their respective sides such that when the indicator line for the patient's scale points to no pain, the indicator line for the provider's scale points to 0. Similarly, when the indicator line for the patient's scale points to unbearable pain, the indicator line for the provider's scale points to 10.

In use, the provider presents the patient's pain scale to the patient and has the patient indicate the amount and intensity of pain the patient is or was experiencing by positioning the indicator at a subjective point along the scale. The patient is not permitted to view the provider's pain scale that shows discrete, incremental intervals corresponding to numerical and/or verbal pain descriptors. The health care provider then reads and records the numerical and/or verbal pain descriptor indicated on the provider's pain scale by the slidable indicator. As described above, the slidable indicator points to a position on the provider's pain scale that is the compliment to the position indicated by the patient on the patient's pain scale.

DETAILED DESCRIPTION OF THE INVENTION

In the following detailed description, the invention will be described in one preferred embodiment. However, the described form is not meant to be exhaustive or to limit the invention to the precise form disclosed. This description is general and is meant to best explain the principles of the invention.

The preferred embodiment of the present invention, a Visual Analog Scale (10), is a rectangular base (16) that has a frontside (12) and a backside (14). The Visual Analog Scale (10), in alternate embodiments, can take other shapes such as a circular base.

Figure 1:
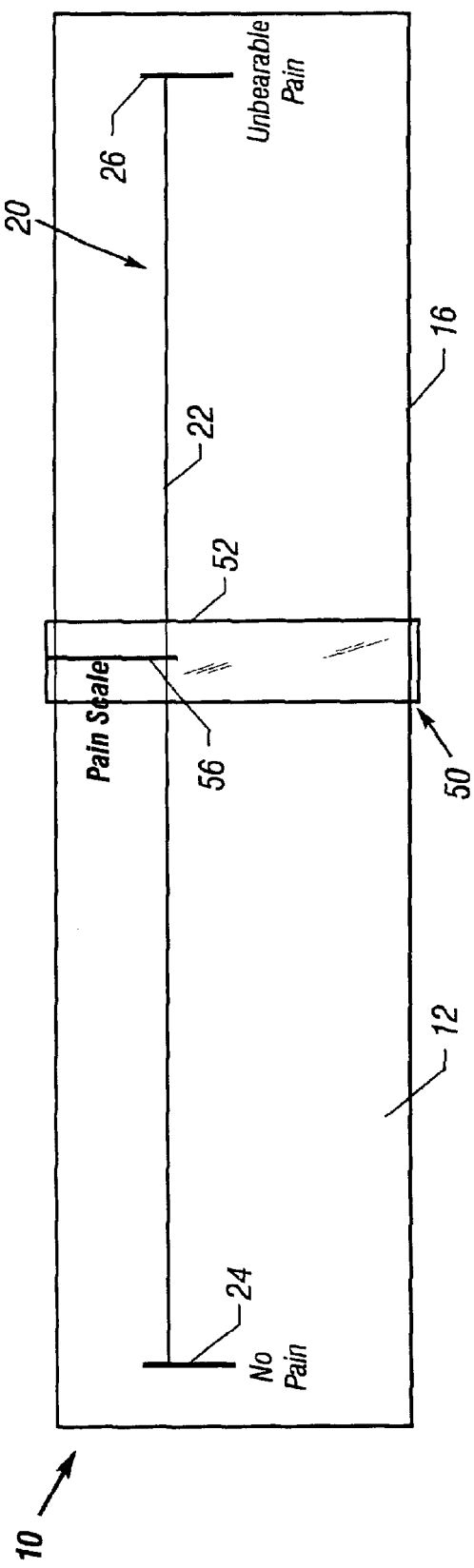
FIG. 1 shows a front view of the visual analog scale of the present invention.

FIG. 1 shows the frontside (12) of the Visual Analog Scale (10). The frontside (12) displays a Patient's Pain Scale (20) that presents a spectrum (22) of pain having a first end (24) and a second end (26). The spectrum (22) is a continuous solid line without markings other than at the first end (22) and the second end (26).

The first end (24) of the spectrum (22) is indicated by a line that is generally perpendicular to the spectrum (22) and that corresponds to the minimum amount of pain that a person can experience (i.e. "No Pain"). In the preferred embodiment, when viewing the frontside (12), the first end (24) of the spectrum (22) is to the viewer's left. The second end (26) of the spectrum (22) is indicated by a line that is generally perpendicular to the spectrum (22) and that corresponds to the maximum amount of pain that a person can experience (i.e. "Unbearable Pain"). In the preferred embodiment, when viewing the frontside (12), the second end (26) of the spectrum (22) is to the viewer's right.

However, in alternate embodiments, the first end (24) and the second end (26) of the spectrum (22) can appear opposite from those positions described above. In another alternate embodiment, the spectrum (22) can be arranged around the perimeter of a Visual Analog Scale having a circular base and can span the entire perimeter or an arc of the circle.

Figure 2:
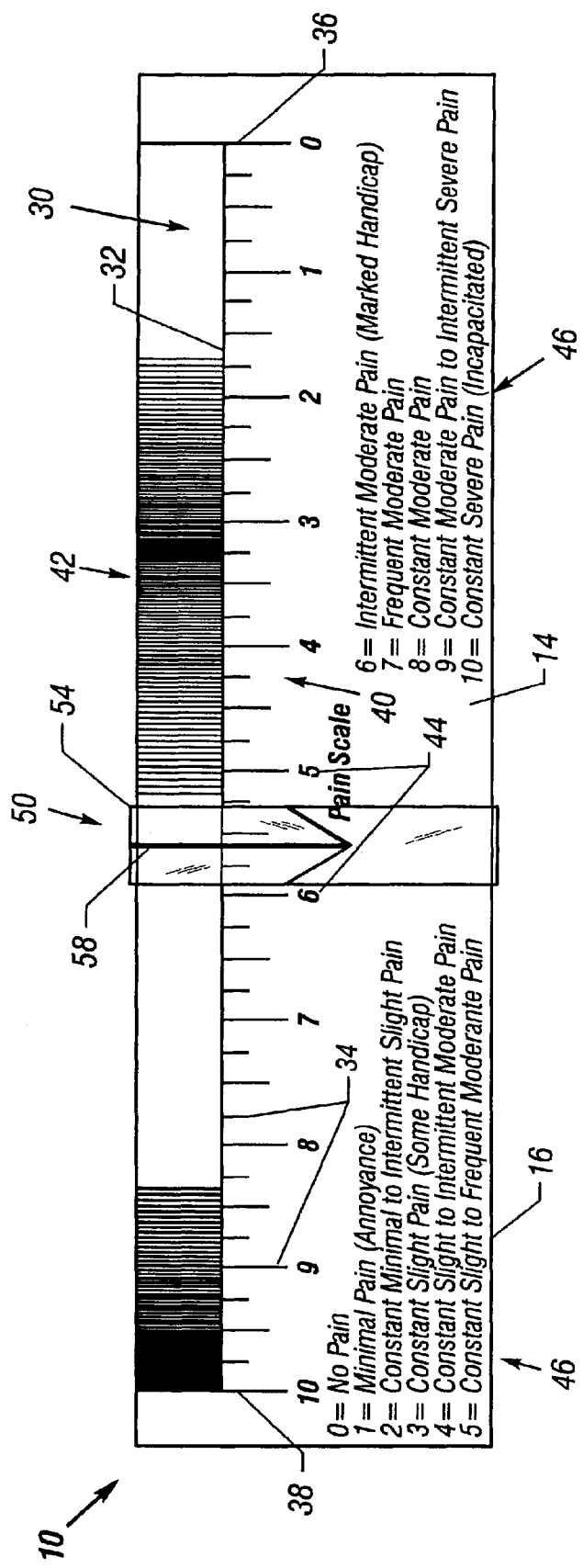
FIG. 2 shows a back view of the visual analog scale of the present invention.

FIG. 2 shows the backside (14) of the Visual Analog Scale (10). The backside (14) displays a Provider's Pain Scale (30) that presents a range of pain descriptors (32) having a first end (36) and a second end (38). The range of pain descriptors (32) is a solid line with markings (34) at uniform discrete intervals between the first end (36) and the second end (38), inclusive, as in a ruler. The first end (36) of the range of pain descriptors (32) corresponds to the low end of the range of pain descriptors (32) and represents the minimum amount of pain that a person can experience (i.e. "No Pain"). In the preferred embodiment, when viewing the backside (14), the first end (36) of the range of pain descriptors (32) is to the viewer's right.

The second end (38) of the range of pain descriptors (32) corresponds to the high end of the range of pain descriptors (32) and represents the maximum amount of pain that a person can experience (i.e. "Constant Severe Pain"). In the preferred embodiment, when viewing the backside (14), the second end (38) of the range of pain descriptors (32) is to the viewer's left. In this way, the range of pain descriptors (32) on the backside (14) is a complement to the spectrum (22) on the frontside (12).

However, in alternate embodiments, the first end (36) and the second end (38) of the range of pain descriptors (32) can appear opposite from those positions described above. In another alternate embodiment, the range of pain descriptors (32) can be arranged around the perimeter of a Visual Analog Scale having a circular base and can span the entire perimeter or an arc of the circle.

In the preferred embodiment, the discrete intervals identified by the markings (34) of the range of pain descriptors (32) are identified by numerical pain descriptors (44). The numerical pain descriptors (44) are numbered from 0 through 10 in increments of 1. The numerical pain descriptors (44) correspond to verbal pain descriptors (46) as follows:

| Numerical Pain Descriptors (44) | Verbal Pain Descriptors (46) |
|---|---|
| 0 | No Pain |
| 1 | Minimal Pain |
| 2 | Constant Minimal to Intermittent Slight Pain |
| 3 | Constant Slight Pain |
| 4 | Constant Slight to Intermittent moderate Pain |
| 5 | Constant Slight to Frequent Moderate Pain |
| 6 | Intermittent Moderate Pain |
| 7 | Frequent Moderate Pain |
| 8 | Constant Moderate Pain |
| 9 | Constant Moderate to Intermittent Severe Pain |
| 10 | Constant Severe Pain |

Verbal Pain Descriptor (46) "Minimal Pain" is equivalent to the patient experiencing an annoyance. Verbal Pain Descriptor (46) "Constant Slight Pain" is equivalent to the patient suffering from some handicap. Verbal Pain Descriptor (46) "Intermittent Moderate Pain" is equivalent to the patient suffering from a marked handicap. Verbal Pain Descriptor (46) "Constant Severe Pain" is equivalent to the patient being incapacitated.

Other embodiments of the backside (14) of the Visual Analog Scale (10) include a color bar (42) above the range of pain descriptors (32). The color bar (42) represents the range of pain that a patient can experience and presents that representation by using colors similar to that of the spectrum of visible light. As the numerical pain descriptor (44) increases from 0 to 10 the colors change as follows: White; Violet; Indigo; Blue; Green; Yellow; Orange; and Red. According to this progression, numerical pain descriptor (44) 0 is represented by the color white and numerical pain descriptor (44) 10 is represented by red.

The present invention also has an indicator (50) that is mounted on the Visual Analog Scale (10). The indicator (50) generally has an elongated shape with a first arm (52) and a second arm (54). The indicator (50) is wrapped around the Visual Analog Scale (10) such that the first arm (52) and second arm (54) are generally perpendicular to the spectrum (22) and range of pain descriptors (32), respectively.

The first arm (52) of the indicator (50) covers at least a portion of the frontside (12) of the Visual Analog Scale (10) and is made from a transparent to translucent material through which the spectrum (22) and any other markings on the frontside (12) can be read. The indicator (50) is slidably movable from the first end (24) of the spectrum (22) to the second end (26) and vice versa. In alternate embodiments, the indicator (50) could rotate around a circular shaped Visual Analog Scale.

The first arm (52) of the indicator (50) bears a translucent to opaque patient's indicator line (56). The patient's indicator line (56) approaches or intersects the spectrum (22) along its entire range as the indicator is moved from the first end (24) to the second end (26). The patient's indicator line (56) operates to point to the place on the spectrum (22) that corresponds to the level of pain that the patient is experiencing.

The second arm (54) of the indicator (50) covers at least a portion of the backside (14) of the Visual Analog Scale (10). The second arm (54) is made from a transparent to translucent material through which the range of pain descriptors (32) and any other markings on the backside (14)

can be read. The indicator (50) is slidably movable from the first end (34) of the range of pain descriptors (32) to the second end (36) and vice versa.

The second arm (54) of the indicator (50) bears a translucent to opaque provider's indicator line (58). The provider's indicator line (58) approaches or intersects the range of pain descriptors (32) along its entire range as the indicator is moved from the first end (34) to the second end (36). The provider's indicator line (58) is connected to the patient's indicator line (56) that appears on the first arm (52) of the indicator (50). The provider's indicator line (58) points to the place on the range of pain descriptors (32) that is the complement to the level of pain that the patient indicated on the spectrum (22) on the frontside (12) of the Visual Analog Scale (10).

The preferred embodiment of the method for using the Visual Analog Scale (10) described above begins with providing the Visual Analog Scale (10) to the patient. The patient is presented with the frontside (12) of the Visual Analog Scale (10) and prevented from seeing the backside (14). The patient indicates the level of pain being experienced by positioning the indicator (50) along the spectrum (22) corresponding to an amount of pain at a point between the first end (24) and the second end (26). The patient's indicator line (56) on the first arm (52) of the indicator (50) points to the place on the spectrum (22) that corresponds to the level of pain being experienced.

The provider then diagnoses the patient's pain by reading the numerical pain descriptor (44) or verbal pain descriptor (46) indicated by the provider's indicator line (58) on the second arm (54) of the indicator (50). The provider's indicator line (58) lines up with the patient's indictor line (56) and indicates the numerical pain descriptor (44) or verbal pain descriptor (46) that is the complement to the level of pain being experienced by the patient as indicated on the frontside (12). In this way, the patient describes the level of pain being experienced without being influenced by suggested verbal or numerical descriptions.

The above-described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A Visual Analog Scale for diagnosing an amount and intensity of pain comprising:

a base having a frontside and a backside;

a patient's pain scale on the frontside of the base;

a provider's pain scale on the backside of the base, said provider's pain scale comprising a range of pain descriptors having a first end and a second end;

an indicator mounted on the base operatively connected to the patient's pain scale; and said indicator operatively connected to the provider's pain scale.

2. The Visual Analog Scale of claim 1 wherein the range of pain descriptors comprises a continuous solid line having markings identifying uniform discrete intervals between the first end and the second end, inclusive.

3. The Visual Analog Scale of claim 1 wherein the first end of the range of pain descriptors corresponds to a minimum amount of pain and the second end of the range of pain descriptors corresponds to a maximum amount of pain.

4. A Visual Analog Scale for diagnosing an amount and intensity of pain comprising:

base having a frontside and a backside;

a patient's pain scale on the frontside of the base, wherein the patient's pain scale comprises a spectrum having a first end and a second end;

a provider's pain scale on the backside of the base, wherein the provider's pain scale comprises a range of pain descriptors having a first end and a second end; and an indicator mounted on the base, wherein the indicator comprises an elongated shape having a first arm and a second arm, a patient's indicator line on the first arm, wherein the first arm is operatively connected to the frontside, and a provider's indicator line on the second arm, wherein the second arm is operatively connected to the backside.

5. A Visual Analog Scale of for diagnosing an amount and intensity of pain comprising:

a base having a frontside and a backside;

a patient's pain scale on the frontside of the base, wherein the patient's pain scale comprises a spectrum having a first end and a second end;

said first end of the spectrum corresponding to a minimum amount of pain and said second end of the spectrum corresponding to a maximum amount of pain;

a provider's pain scale on the backside of the base, wherein the provider's pain scale comprises a range of pain descriptors having a first end and a second end; and an indicator mounted on the base, wherein the indicator comprises an elongated shape having a first arm and a second arm, a patient's indicator line on the first arm, wherein the first arm is operatively connected to the frontside, and a provider's indicator line on the second arm, wherein the second arm is operatively connected to the backside.

6. The Visual Analog Scale of claim 4 wherein the first end of the range of pain descriptors corresponds to a minimum amount of pain and the second end of the range of pain descriptors corresponds to a maximum amount of pain.

7. The Visual Analog Scale of claim 5 wherein the range of pain descriptors comprises a solid line having uniform discrete intervals identified by markings between the first end and the second end, inclusive.

8. The Visual Analog Scale of claim 7 wherein the markings correspond to numerical pain descriptors.

9. The Visual Analog Scale of claim 7 wherein the markings correspond to verbal pain descriptors.

10. The Visual Analog Scale of claim 5 wherein the indicator is complementarily connected to the provider's pain scale and the patient's pain scale.

11. A Visual Analog Scale for diagnosing an amount and intensity of pain comprising:

a base having a frontside and a backside;

a patient's pain scale on the frontside of the base comprising a spectrum having a first end and a second end, wherein the first end of the spectrum corresponds to a minimum amount of pain and the second end of the spectrum corresponds to a maximum amount of pain;

a provider's pain scale on the backside of the base comprising a range of pain descriptors having a first end and a second end, wherein the first end of the range of pain descriptors corresponds to a minimum amount of pain and the second end of the range of pain descriptors corresponds to a maximum amount of pain; and an indicator mounted on the base and operatively connected to the provider's pain scale and the patient's pain scale, wherein the indicator comprises an elongated shape having a first arm and a second arm, a patient's indicator line on the first arm, wherein the first arm is operatively connected to the frontside, and a provider's indicator line on the second arm, wherein the second arm is operatively connected to the backside.

12. The Visual Analog Scale of claim 11 wherein the range of pain descriptors comprises a solid line having uniform discrete intervals identified by markings between the first end and the second end, inclusive.

13. The Visual Analog Scale of claim 12 wherein the markings correspond to numerical pain descriptors.

14. The Visual Analog Scale of claim 12 wherein the markings correspond to verbal pain descriptors.

15. A method for accurately diagnosing an amount and intensity of pain being experienced by a person comprising:
  providing a visual analog scale to the patient, wherein the visual analog scale comprises a base having a frontside and a backside, a patient's pain scale on the frontside, a provider's pain scale on the backside wherein the provider's pain scale is a range of pain descriptors comprising a continuous solid line having markings identifying uniform discrete intervals, and an indicator mounted on the base operatively connected to both the patient's pain scale and the provider's pain scale;
  causing the patient to adjust the indicator operatively connected to the patient's pain scale to indicate on the patient's pain scale the amount and intensity of pain being experienced;
  observing the amount and intensity of pain indicated on the provider's pain scale by the operation of the indicator on the provider's pain scale to provide an accurate diagnosis of the amount and intensity of the pain being experienced without influencing the patient's description of the pain being experienced.

16. The method of claim 15 further comprising preventing the patient from observing the provider's pain scale.

17. The method of claim 15 further comprising assigning numerical pain descriptors to the markings on the provider's pain scale to provide an accurate diagnosis of the amount and intensity of the pain being experienced without influencing the patient's description of the pain being experienced.

18. The method of claim 15 further comprising assigning verbal pain descriptors to the markings on the provider's pain scale to provide an accurate diagnosis of the amount and intensity of the pain being experienced without influencing the patient's description of the pain being experienced.

19. A method for accurately diagnosing an amount and intensity of pain being experienced by a person comprising:
  providing a visual analog scale to the patient, wherein the visual analog scale comprises a base having a frontside and a backside, a patient's pain scale on the frontside, a provider's pain scale on the backside wherein the provider's pain scale is a range of pain descriptors comprising a continuous solid line having markings identifying uniform discrete intervals, and an indicator mounted on the base operatively connected to both the patient's pain scale and the provider's pain scale;
  preventing the patient from observing the provider's pain scale;
  causing the patient to adjust the indicator operatively connected to the patient's pain scale to indicate on the patient's pain scale the amount and intensity of pain being experienced;
  observing the amount and intensity of pain indicated on the provider's pain scale by the operation of the indicator on the provider's pain scale to provide an accurate diagnosis of the amount and intensity of the pain being experienced without influencing the patient's description of the pain being experienced.

20. The method of claim 19 further comprising assigning numerical pain descriptors to the markings on the provider's pain scale to provide an accurate diagnosis of the amount and intensity of the pain being experienced without influencing the patient's description of the pain being experienced.

21. The method of claim 19 further comprising assigning verbal pain descriptors to the markings on the provider's pain scale to provide an accurate diagnosis of the amount and intensity of the pain being experienced without influencing the patient's description of the pain being experienced.

\* \* \* \* \*